US00RE49359E

(19) United States
(12) Reissued Patent
Verbeek

(10) Patent Number: US RE49,359 E
(45) Date of Reissued Patent: Jan. 10, 2023

(54) INSTRUMENT FOR ENDOSCOPIC APPLICATIONS OR THE LIKE

(71) Applicant: Fortimedix Assets II B.V., Geleen (NL)

(72) Inventor: Marcel Antonius Elisabeth Verbeek, Heerlen (NL)

(73) Assignee: Fortimedix Assets II B.V., Geleen (NL)

(21) Appl. No.: 16/722,094

(22) Filed: Dec. 20, 2019

Related U.S. Patent Documents

Reissue of:
(64) Patent No.: 9,848,858
Issued: Dec. 26, 2017
Appl. No.: 14/221,710
Filed: Mar. 21, 2014

U.S. Applications:
(62) Division of application No. 12/933,703, filed as application No. PCT/EP2008/003133 on Apr. 18, 2008, now Pat. No. 8,740,884.

(51) Int. Cl.
*A61B 17/00* (2006.01)
*A61B 1/005* (2006.01)
(Continued)

(52) U.S. Cl.
CPC ..... *A61B 17/00234* (2013.01); *A61B 1/005* (2013.01); *A61B 1/0052* (2013.01);
(Continued)

(58) Field of Classification Search
CPC ..... A61B 17/00234; A61B 1/00135; A61B 1/005; A61B 1/0052; A61B 1/0055;
(Continued)

(56) References Cited

U.S. PATENT DOCUMENTS 5,769,841 A 6/1998 Odell et al.
6,053,907 A * 4/2000 Zirps ..... A61B 17/32002 604/20
(Continued)

FOREIGN PATENT DOCUMENTS

DE 10 2007 019 779 A1 10/2007
DE 102007019779 A1 10/2007
(Continued)

OTHER PUBLICATIONS

International Search Report issued Jan. 22, 2009 in International (PCT) Application No. PCT/EP2008/003133.

*Primary Examiner* — Catherine S Williams
(74) *Attorney, Agent, or Firm* — N.V. Nederlandsch Octrooibureau

(57) ABSTRACT

An instrument for endoscopic applications, including a tubular member having a handling end portion having a flexible portion and actuating devices located at the other end portion, and longitudinal elements for transferring the movement of the actuating devices to the handling end portion resulting in a change of orientation thereof, whereby the handling end portion includes at least two independent flexible portions, whereby the actuating end portion has a corresponding number of actuating devices, and whereby each actuating device is connected by its own set of longitudinal elements to a part of the handling end portion for effecting a change of orientation of one of the flexible portions.

15 Claims, 10 Drawing Sheets

(51) Int. Cl.

| | |
|---|---|
| ***A61M 25/01*** | (2006.01) |
| ***B25J 18/06*** | (2006.01) |
| ***A61B 1/00*** | (2006.01) |
| *A61M 25/00* | (2006.01) |

(52) U.S. Cl.

CPC ..... *A61B 1/0055* (2013.01); *A61B 1/00135* (2013.01); *A61M 25/0136* (2013.01); *A61M 25/0138* (2013.01); *A61M 25/0147* (2013.01); *B25J 18/06* (2013.01); *A61B 2017/00309* (2013.01); *A61M 25/0045* (2013.01); *A61M 25/0054* (2013.01); *A61M 2025/0161* (2013.01); *Y10T 74/20323* (2015.01)

(58) Field of Classification Search

CPC .... A61B 2017/00309; A61M 25/0136; A61M 25/0138; A61M 25/0147; A61M 25/0045; A61M 25/0054; A61M 2025/0161; B25J 18/06; Y10T 74/20323

See application file for complete search history.

(56) References Cited

U.S. PATENT DOCUMENTS

| | | | | |
|---|---|---|---|---|
| 6,086,773 | A | 7/2000 | Dufresne et al. | |
| 6,107,004 | A | 8/2000 | Donadio, III | |
| 6,485,411 | B1 | 11/2002 | Konstorum et al. | |
| 6,537,459 | B1 | 3/2003 | Dufresne et al. | |
| 7,018,330 | B2 | 3/2006 | Alekseenko et al. | |
| 7,169,141 | B2 | 1/2007 | Brock et al. | |
| 7,637,905 | B2 * | 12/2009 | Saadat | A61B 1/0055 600/104 |
| 7,725,214 | B2 | 5/2010 | Diolaiti | |
| 7,744,608 | B2 | 6/2010 | Lee et al. | |
| 7,862,554 | B2 | 1/2011 | Hegeman et al. | |
| 7,942,868 | B2 | 5/2011 | Cooper | |
| 8,105,350 | B2 | 1/2012 | Lee et al. | |
| 8,182,415 | B2 | 5/2012 | Larkin et al. | |
| 8,251,977 | B2 * | 8/2012 | Partlett | A61M 25/0105 604/523 |
| 2002/0062063 | A1 | 5/2002 | Ogura et al. | |
| 2002/0068868 | A1 * | 6/2002 | Thompson | A61M 25/0152 600/434 |
| 2003/0036748 | A1 * | 2/2003 | Cooper | A61B 17/00234 606/1 |
| 2003/0069522 | A1 | 4/2003 | Jacobsen et al. | |
| 2003/0149338 | A1 | 8/2003 | Francois et al. | |
| 2003/0225392 | A1 * | 12/2003 | McMichael | A61J 15/0069 604/509 |
| 2004/0138527 | A1 * | 7/2004 | Bonner | A61B 46/00 600/114 |
| 2004/0138700 | A1 * | 7/2004 | Cooper | A61B 17/00 606/205 |
| 2004/0193021 | A1 * | 9/2004 | Zdeblick | A61B 5/036 600/300 |
| 2005/0027287 | A1 | 2/2005 | O'Connor et al. | |
| 2005/0107667 | A1 * | 5/2005 | Danitz | A61B 17/07207 600/139 |
| 2005/0203382 | A1 * | 9/2005 | Govari | A61B 34/20 600/424 |
| 2005/0216033 | A1 * | 9/2005 | Lee | A61B 90/36 606/130 |
| 2005/0273085 | A1 | 12/2005 | Hinman et al. | |
| 2006/0111616 | A1 * | 5/2006 | Danitz | A61B 1/0055 600/142 |
| 2006/0241564 | A1 * | 10/2006 | Corcoran | A61M 25/0138 604/523 |
| 2006/0281566 | A1 | 12/2006 | Lee | |
| 2007/0049800 | A1 | 3/2007 | Boulais | |
| 2007/0135803 | A1 | 6/2007 | Belson | |
| 2007/0219581 | A1 * | 9/2007 | Dohi | A61B 17/29 606/205 |
| 2007/0299424 | A1 * | 12/2007 | Cumming | A61M 25/0012 604/527 |
| 2008/0051802 | A1 | 2/2008 | Schostek et al. | |
| 2008/0234545 | A1 * | 9/2008 | Breedveld | A61B 17/29 600/104 |
| 2008/0262480 | A1 | 10/2008 | Stahler et al. | |
| 2008/0262538 | A1 * | 10/2008 | Danitz | A61B 1/0053 606/205 |
| 2009/0069632 | A1 * | 3/2009 | McIntyre | A61B 1/00098 600/146 |
| 2009/0131865 | A1 * | 5/2009 | Partlett | A61M 25/0009 604/95.04 |
| 2009/0299343 | A1 | 12/2009 | Rogers | |
| 2011/0004157 | A1 * | 1/2011 | Dewaele | A61B 1/00071 604/95.01 |
| 2011/0034764 | A1 | 2/2011 | Verbeek | |

FOREIGN PATENT DOCUMENTS

| | | | |
|---|---|---|---|
| EP | 0 916 359 | A1 | 5/1999 |
| EP | 1 708 609 | | 10/2006 |
| EP | 1 709 987 | | 10/2006 |
| EP | 1708609 | A1 | 10/2006 |
| EP | 1709987 | A1 | 10/2006 |
| JP | 55-148528 | | 11/1980 |
| JP | 01-175827 | | 7/1989 |
| JP | 2-71501 | | 5/1990 |
| JP | 5-20702 | | 3/1993 |
| JP | 09/084753 | | 3/1997 |
| JP | 11-032977 | | 2/1999 |
| JP | 11-239617 | | 9/1999 |
| JP | 11-239617 | A1 | 9/1999 |
| JP | 2002-177202 | | 6/2002 |
| JP | 2002-177202 | A | 6/2002 |
| JP | 2003-159214 | | 6/2003 |
| JP | 2007-516042 | | 6/2007 |
| JP | 2007-516042 | A | 6/2007 |
| JP | 2011-504323 | | 2/2011 |
| WO | 97/42910 | A1 | 11/1997 |
| WO | WO 97/42910 | | 11/1997 |
| WO | 99/61261 | A1 | 12/1999 |
| WO | WO 99/61261 | | 12/1999 |
| WO | 2005/065555 | A1 | 7/2005 |
| WO | 2005/067785 | A1 | 7/2005 |
| WO | WO 2005/065555 | | 7/2005 |
| WO | WO 2005/067785 | | 7/2005 |
| WO | 2005/120326 | A2 | 12/2005 |
| WO | WO 2005/120326 | | 12/2005 |
| WO | 2006/012668 | A1 | 2/2006 |
| WO | WO 2006/012668 | | 2/2006 |
| WO | 2006/057702 | A1 | 6/2006 |
| WO | WO 2006/057702 | | 6/2006 |
| WO | 2009/035812 | A1 | 3/2009 |
| WO | WO 2009/035812 | | 3/2009 |

* cited by examiner

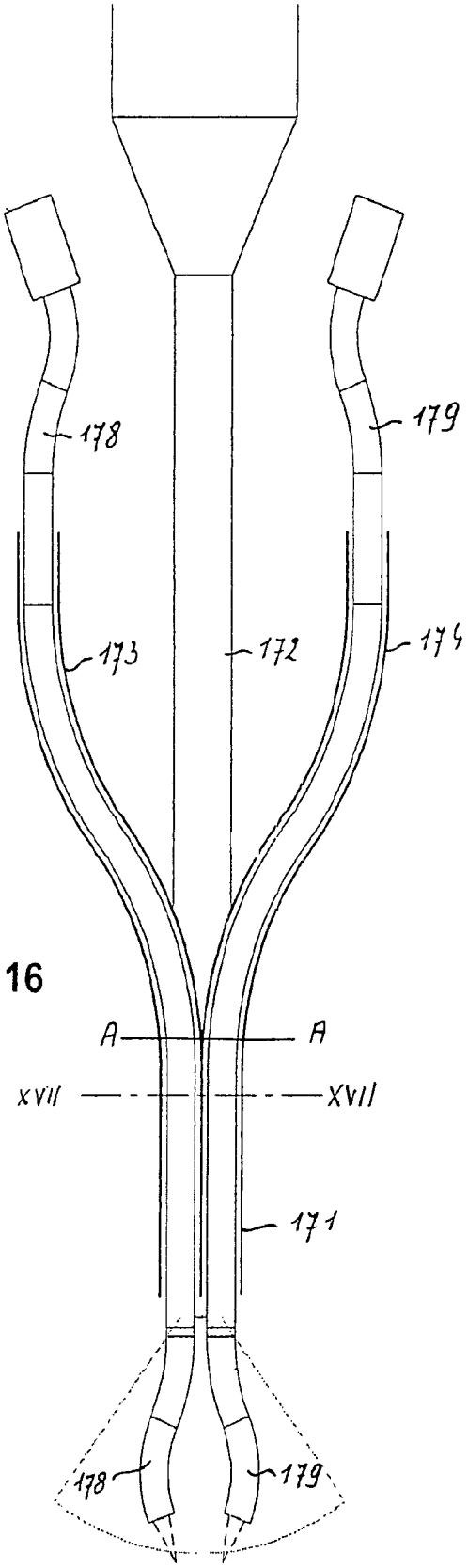
Fig. 16
Fig. 17
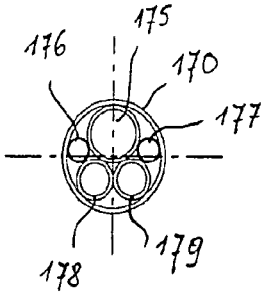

INSTRUMENT FOR ENDOSCOPIC APPLICATIONS OR THE LIKE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

BACKGROUND OF THE INVENTION

I. Technical Field

The invention relates to an instrument for endoscopic applications or the like, comprising a tube like member having a handling end portion having a flexible portion and actuating means located at the other end portion, and longitudinal elements for transferring the movement of the actuating means to the handling end portion resulting in a change of orientation thereof.

II. Description of the Related Art

Such an instrument is known from EP-A-1 708 609 and is normally used for applications such as minimal invasive surgery, but it is also applicable for other purposes such as the inspection or reparation of mechanical or electronic installations at locations which are difficult to reach.

In this known instrument a bending movement of the actuating end portion is transferred to a handling end portion by means of the longitudinal elements resulting in a corresponding bending movement of the handling end portion especially of the flexible part thereof. As a result of this construction the bending orientation of the flexible portion is limited to one direction at a time, as a result of which the application of this type of instrument is limited. This is especially true in situations where two endoscopic instruments are used in a parallel fashion located side by side, as in this situation it is not possible to direct the handling end portion to the same point because of the mutual spherical hindrance. Furthermore it is not always possible to use the instrument at defined locations because of some obstacles present in the access road to the point where some action is needed. More specifically there is a need for an instrument for endoscopic applications or the like which offers advanced possibilities in the guidance of the handling end portion of the instrument.

SUMMARY OF THE INVENTION

It is therefore an object of the invention to provide an instrument of the above named type which avoids the above cited problems and offers more versatile application possibilities.

This and other objects are obtained in that the handling end portion comprises at least two independent flexible portions, in that the actuating end portion has a corresponding number of actuating means, and in that each actuating means is connected by means of its own set of longitudinal elements to a part of the handling end portion for effecting a change of orientation of one of the flexible portions.

As a result of the fact that the handling end portion contains at least two independently controllable flexible portions it becomes possible to make more complicated curves allowing better access to difficult places and more versatile use of the instrument. For instance in case of two flexible portions in the handling end portion it is possible to make S-curves allowing to use parallel endoscope instrument in approaching the same point of operation.

BRIEF DESCRIPTION OF THE DRAWINGS

Other characteristics and advantages of the invention will become clear from the following description reference being made to the annexed drawings. In the drawing is.

DETAILED DESCRIPTION OF THE INVENTION

The instrument as shown in the annexed drawings can be used for endoscopic medical applications, but its use is not restricted to that, as it may be used in other applications, such as technical applications for handling or viewing parts of machines or installations which are otherwise difficult to reach. Endoscopic instrument as used in this description will include also these applications.

Figure 1:
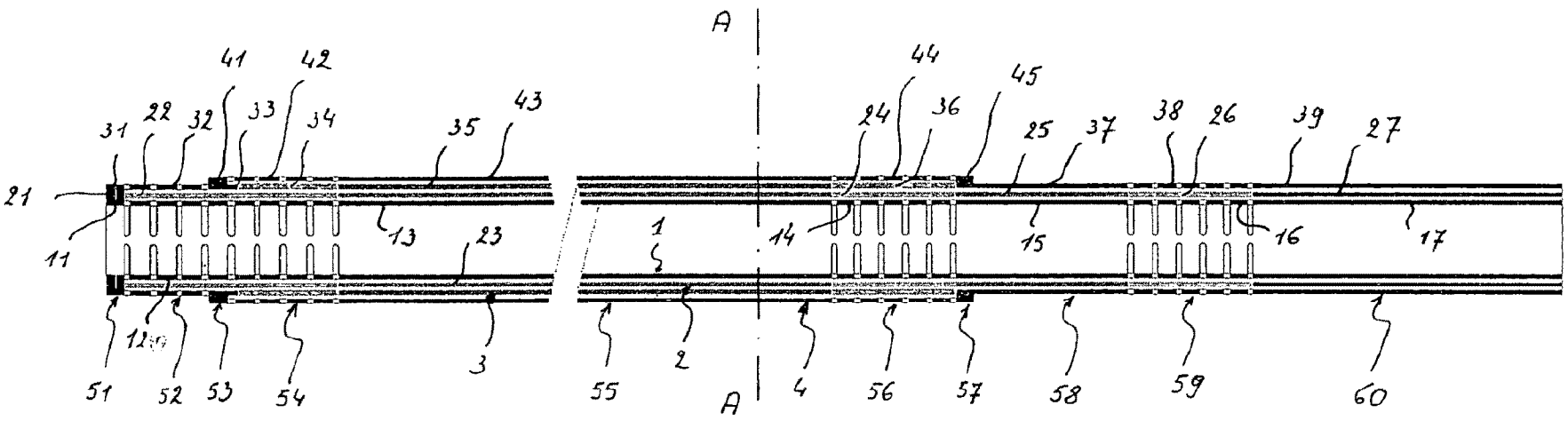
FIG. 1 a schematic cross-section view of an instrument according to the invention, FIG. 2 a schematic cross-section view of the instrument of FIG. 1 showing a first step of its operation, FIG. 3 a schematic cross-section view of the instrument of FIG. 1, showing the second step of its operation, FIG. 4 a schematic cross-section view showing a with respect to FIG. 1 modified embodiment of an instrument according to the invention, FIG. 5 a schematic cross-section view showing a with respect to FIG. 4 modified embodiment of an instrument according to the invention, FIG. 6 a schematic cross-section view showing a with respect to FIGS. 4 and 5 modified embodiment of an instrument according to the invention, FIG. 7 a perspective view of an actuator to be used in an instrument according to the invention, FIG. 8 a perspective view of a modified embodiment of an actuator to be used in a instrument according to the invention, FIG. 9 a schematic cross-section view of an embodiment of an instrument according to the invention having a four level control system, FIG. 10 a schematic view of the instrument according to FIG. 9 in the neutral position, FIG. 11 a schematic view of the instrument according to FIG. 9 with one level of the control system activated, FIG. 12 a schematic view of the instrument according to FIG. 9 with two levels of the control system activated, FIG. 13 a schematic view of the instrument according to FIG. 9 with all four levels of the control system activated, FIG. 14 a schematic perspective view of a part of an instrument according to the invention with four levels of actuation in which the four levels are located within the same layer or cylindrical element, FIG. 15 a schematic perspective view of the instrument of FIG. 14 with part of the external layer or cylindrical element removed, FIG. 16 a schematic drawing of a possible application of the instrument in an endoscopic application, FIG. 17 a cross section according to the line XVII-XVII in FIG. 16, FIG. 18 a schematic perspective view of a part of an instrument according to the invention with eight levels of actuation in which four levels are located in a first layer or cylindrical element and the four remaining levels are located in another layer or cylindrical element, FIG. 19 a schematic perspective view of the instrument of FIG. 18 with part of the external layer or cylindrical element removed, FIGS. 20A, B, C and D schematic views of an application of the endoscopic instrument according to the invention, FIGS. 21A, B, C and D schematic view of a modified embodiment in an application of the endoscopic instrument according to the invention, FIG. 22 a schematic cross-section of an instrument according to the invention, FIG. 23 an exploded view of the three cylindrical members forming the instrument according to the invention, and FIG. 24 an unrolled view of a part of the intermediate cylindrical member of the instrument according to the invention.

The instrument as shown in FIG. 1 comprises four layers or cylindrical elements, a first internal layer or cylindrical element 1, a second intermediate layer or cylindrical element 2, a third intermediate layer or cylindrical element 3 and a fourth external layer or cylindrical element 4, the four elements 1, 2, 3 and 4 being co-axial and surrounding each other as shown.

The first internal layer or cylindrical element 1 as seen along its length is composed of a first rigid ring 11, which is the handling end portion, which means that this portion is used at a remote place which is difficult to reach to perform some action, a first flexible portion 12, a first intermediate rigid portion 13, a second flexible portion 14, a second intermediate rigid portion 15, a third flexible portion 16 and a second rigid end portion 17, which is used as the actuating end portion of the instrument, which means that this end portion is used to control the movement of the other end portion 11.

The first or inner intermediate layer or cylindrical element 2 is as seen along its longitudinal direction composed of a first rigid ring 21, a first flexible portion 22, a first intermediate rigid portion 23, a second flexible portion 24, a second intermediate rigid portion 25, a third flexible portion 26 and a second rigid end portion 27. The longitudinal dimension of the first rigid portion 21, the first flexible portion 22, the first intermediate rigid portion 23, the second flexible portion 24, the second intermediate rigid portion 25, the third flexible portion 26 and the second rigid end portion 27 are approximately equal to the longitudinal dimension of the first rigid portion 11, the first flexible portion 12, the first intermediate rigid portion 13, the second flexible portion 14, the second intermediate rigid portion 15, the third flexible portion 16 and the second rigid end portion 17 respectively and are coinciding with these portions as well.

The second intermediate layer or cylindrical element 3 is as seen along its longitudinal direction composed of a first rigid ring 31, a first flexible portion 32, a second rigid ring 33, a flexible portion 34, a first intermediate rigid portion 35, a first intermediate flexible portion 36, a second intermediate rigid portion 37, a second intermediate flexible portion 38 and a second rigid end portion 39. The longitudinal length of the first rigid end portion 31, the first flexible portion 32 together with the second rigid ring 33 and the second flexible portion 34, the first intermediate rigid portion 35, the first intermediate flexible portion 36, the second intermediate rigid portion 37, the second intermediate flexible portion 38 and the second rigid end portion 39 are approximately equal to the longitudinal dimension of the first rigid ring 11, the first flexible portion 12, the first intermediate rigid portion 13, the second flexible portion 14, the second intermediate rigid portion 15, the third flexible portion 16 and the second rigid end portion 17 respectively and are coinciding with these portions as well.

The fourth external cylindrical element 4 is as seen along its longitudinal direction composed of a first rigid ring 41, a first flexible portion 42, a first intermediate rigid portion 43, a second flexible portion 44, a second rigid ring 45. The longitudinal length of the first flexible portion 42, the first intermediate rigid portion 43 and the second flexible portion 44 are approximately equal to the longitudinal dimension of the second flexible portion 33, the first intermediate rigid portion 34 and the first intermediate flexible portion 35 respectively and are coinciding with these portions as well. The rigid rings 41 and 45 can have only a very limited length and the ring 41 has approximately the same length as the ring 33 and is connected thereto, whereas the ring 45 extends only over the rigid portion 37 with a length which is sufficient to make an adequate connection between the portions 45 and 37 respectively. The end faces of the rigid rings 11, 21 and 31 can be connected to each other and the same applies to the end faces of the end portions 17, 27 and 39.

The internal and external diameters of the cylindrical elements 1, 2, 3 and 4 are chosen in such a way that the external diameter of the element 1 is almost equal to the internal diameter of the element 2, the external diameter of the element 2 is almost equal to the internal diameter of element 3 and the external diameter of the element is almost equal to the internal diameter of the element 4, in such a way that a sliding movement of the adjacent elements with respect to each other is possible. The flexible elements 12, 42, 14, 44, 16 and 38 can be obtained by the methods described in the European patent application 08 004 373.0 filed on Oct. 3, 2008, page 5, lines 15-26, but any other suitable process can be used to make flexible portions. Otherwise the portions 22, 23, 24, 25, 26 and 34, 35, 36 are comparable to the longitudinal elements described in the above mentioned European patent application for transferring the movement of one portion of the endoscopic instrument to another portion or ring. Any embodiment described in that patent application can be used according to the invention. Otherwise the longitudinal elements can also be obtained by any other system known in the art such as for example described in EP-A-1 708 609. The only applicable restriction with respect to the construction of the longitudinal elements used in these portions is that the total flexibility of the instrument in these locations where the flexible portions coincide must be maintained.

The different layers or cylindrical elements as described above may be produced by any of the known processes, provided that they are suitable to make a multilayer system. Under multilayer it must be understood an endoscopic instrument having at least two separate systems of longitudinal elements for transferring the movement of the actuating end portion to the handling portion. The assembling of the different cylindrical elements can be performed in the same way as well. Preferred processes for producing the different cylindrical elements have been described in the above mentioned European patent application 08 004 373.0 filed on Oct. 3, 2008 which is here incorporated by reference.

Figure 22:
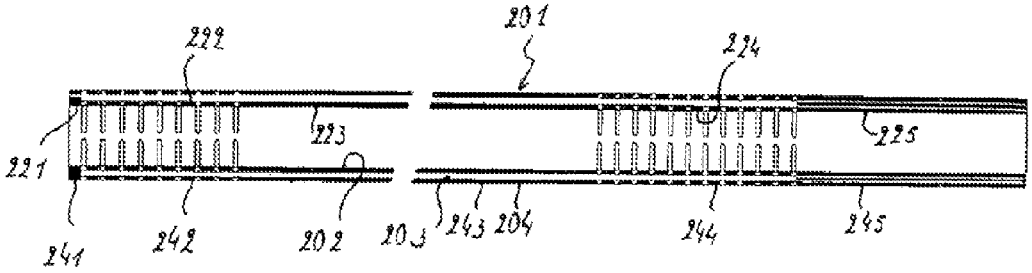

In FIG. 22 there is shown an axial cross-section of an instrument 201 according to the invention. The instrument 201 is composed of three coaxial cylindrical members an inner member 202, an intermediate member 203 and an outer member 204. The inner cylindrical member 202 is composed of a first rigid end part 221, which is the part normally used at the location which is difficult to reach or inside the human body or, a first flexible part 222, an intermediate rigid part 223, a second flexible part 224 and a second rigid end part 225 which is normally used as the operating part of the instrument in that it serves to steer the other end of the unit. The outer cylindrical member 204 is in the same way composed of a first rigid part 241, a flexible part 242, an intermediate rigid part 243, a second flexible part 244 and a second rigid part 245. The length of the different parts of the cylindrical members 202 and 204 are substantially the same so that when the cylindrical member 202 is inserted into the cylindrical member 204, the different parts are positioned against each other. The intermediate cylindrical member 203 also has a first rigid end part 231 and a second rigid end part 235 which in the assembled condition are located between the corresponding rigid parts 221, 241 and 225, 245 respectively of the two other cylindrical members.

The intermediate part 233 of the intermediate cylindrical member is formed by three or more separate longitudinal elements which can have different forms and shapes as will be explained below. After assembly of the three cylindrical members 202, 203 and 204 whereby the member 202 is inserted in the member 203 and the two combined members 202, 203 are inserted into the member 204, the end faces of the three members 202, 203 and 204 are connected to each other at both ends so as to have one integral unit.

Figure 23:
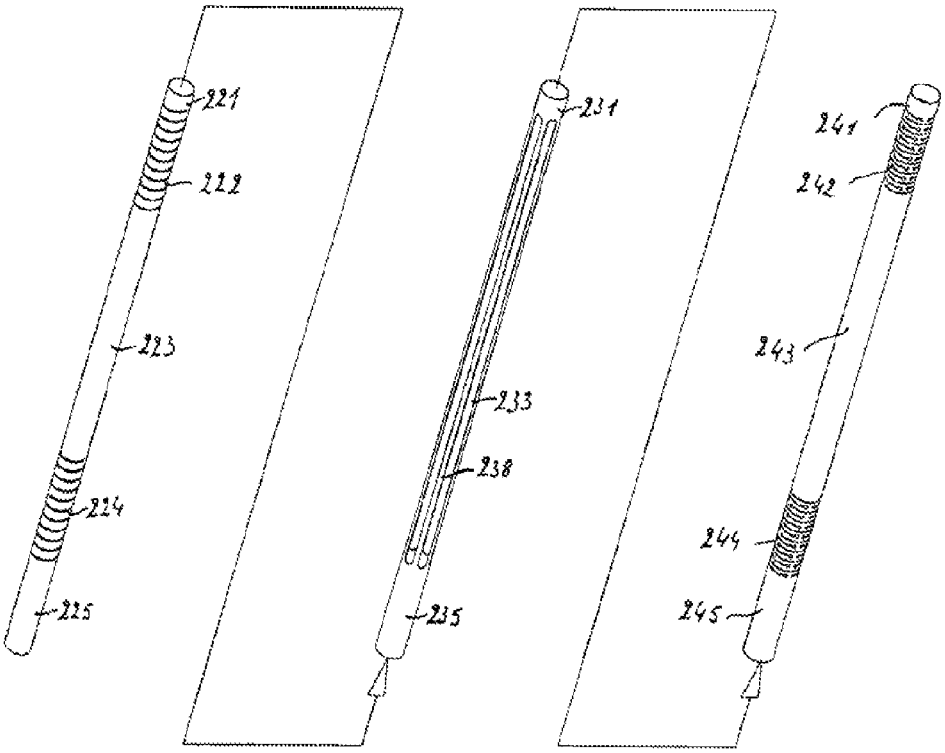
Figure 24:
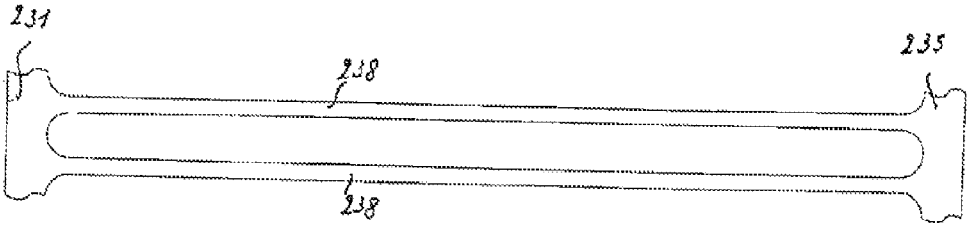

In the embodiment shown in FIG. 23 the intermediate part 233 is formed by a number of longitudinal elements 238 with a uniform cross-section so that the intermediate part 233 has the general shape and form as shown in the unrolled condition in FIG. 24. From this it also becomes clear that the intermediate part is formed by a number of over the circumference of the cylindrical part 203 equally spaced parallel longitudinal elements 238. The number of elements 238 must be at least three, so that the instrument 1 becomes fully controllable in any direction, but any higher number is possible as well.

The production of such an intermediate part is most conveniently done by injection moulding or plating techniques or starting form a regular cylindrical tube with the desired inner and outer diameter and removing these parts of the tube wall required to end up with the desired shape of the intermediate cylindrical member. This removal of material can be done by means of different techniques such as laser cutting, photochemical etching, deep pressing, conventional chipping techniques such as drilling or milling, high pressure water jet cutting systems or any suitable material removing process available. Preferably laser cutting is used as this allows a very accurate and clean removal of material under reasonable economic conditions. These are convenient ways as the member 203 can be made so to say in one process, without requiring additional steps for connecting the different parts of the intermediate cylindrical member as was required in the conventional instruments, where the longitudinal members must be connected in some way to the end parts.

The use of the construction as described above allows the instrument to be used for double bending as will be explained with respect to the FIGS. 2 and 3.

For convenience reasons the different portions of the cylindrical elements have been named according to zones 51-60, in which zone 51 is formed by the rigid rings 11, 21 and 31. Zone 52 is formed by the portion 32 and the parts of the portions 12 and 22 coinciding therewith. Zone 53 is formed by the rings 33 and 41 and the part of the portions 12 and 22 coinciding therewith. Zone 54 is formed by the portions 34 and 42 and the part of the portions 12 and 22 coinciding therewith. Zone 55 is formed by the portions 13, 23, 35 and 43. Zone 56 is formed by the portions 14, 24, 36 and 44, zone 57 is formed by ring 45 and by the part of the portions 15, 25 and 37 coinciding therewith. Zone 58 is formed by the portion 37 and the part of the portions 15 and 25 coinciding therewith. Zone 59 is formed by the portions 16, 26 and 38 and zone 60 is formed by the portions 17, 27 and 39.

Figure 2:
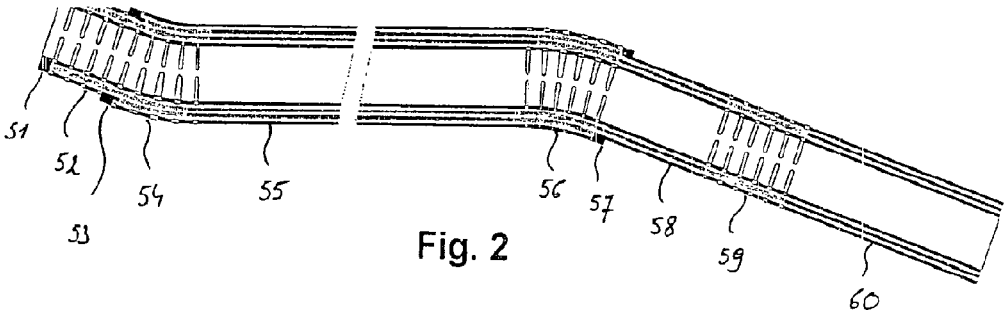

For operating the handling end portion of the endoscopic instrument as shown in FIG. 2, it is possible to apply a bending force, in any radial direction, to the zone 58 so as to bend the zone 56. In view of the connection by means of longitudinal elements formed by the portions 34, 35 and 36 between the portion 37 and the ring 33 this bending deformation of the zone 56 is transferred by longitudinal displacement of portion 35, into a bending deformation in the zone 54 as shown.

The bending of the portion 24, and therefore the longitudinal displacement of portion 23, as a result of bending zone 56, is fully absorbed by bending of portion 22 where it coincides with the portion 33 and will therefore not result in any deformation of the remaining of the portion 22 coinciding with the zone 52.

Figure 3:
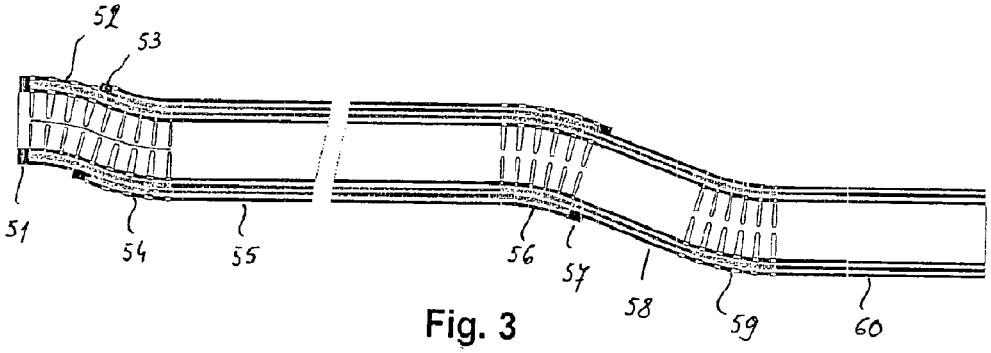

When subsequently and as shown in FIG. 3 a bending force, in any radial direction, is applied to the zone 60 whereby the zone 59 is bended as shown, this will result in the bending of the zone 52, which is due to the connection by means of longitudinal elements formed by the portions 22, 23, 24, 25 and 26 between the ring 21 and the portion 27. The initial bending of the instrument in zone 54 will be maintained because this bending is directed by zone the bending of zone 56. This is why at the handling end of the instrument a double bending is obtained caused by the individual bendings of the zones 52 and 54. In this way it becomes possible to give the handling head of the instrument a position and longitudinal axis direction that are independent from each other. In known instruments such as described in EP-A-1 708 609 the position and the direction of the longitudinal axis are always coupled and can not be individually controlled.

Obviously, it is possible to vary the length of the flexible portions as to accommodate specific requirements with regard to bending radii and total lengths of the handling end and actuating end or to accommodate amplification ratios between bending of the actuating end and the handling end.

Figure 4:
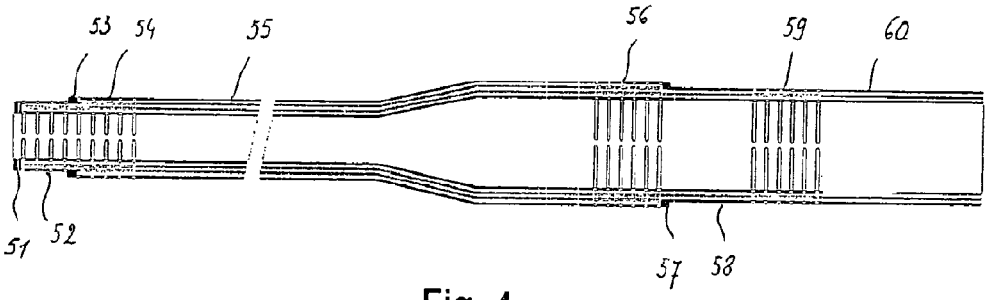

In FIG. 4 there is shown a modified embodiment of the instrument according to the invention. In this embodiment there is shown an instrument having four layers and as such the instrument is comparable to the instrument of FIG. 1 but the actuating portion of the cylindrical elements has a larger diameter compared to the handling end portion and in the zone 56 a frusto-conical part has been incorporated. As a result of the larger diameter of the actuating portion the movement of the handling portion will be amplified upon bending thereby amplifying the movement of the handling head. It is also possible to work in the opposite direction with a handling portion with a larger diameter than the actuating portion whereby the degree of movement is decreased, thereby improving accuracy of movement of the handling head In FIG. 5 there is shown an embodiment of an instrument according to the invention which is comparable to the instrument as shown in FIG. 4 in which the movement of the actuating portions is amplified into a movement of the handling portion. Here also there is shown an instrument having four layers as in the instrument of FIG. 1.

Figure 5:
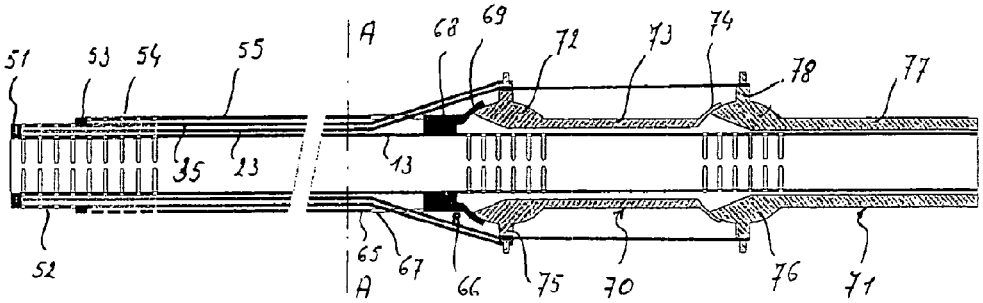

The left hand side with respect to the line A-A of the instrument as shown in FIG. 5, which is the handling end portion, is completely identical to the left hand side with respect to the line A-A of the instrument as shown in FIG. 1. The right hand side with respect to the line A-A of the instrument as shown in FIG. 5 has been modified. The inner layer or cylindrical element 1 can be completely identical to the inner layer 1 shown in FIG. 1. The outer layer or cylindrical element at the right hand side of the line A-A has been modified in that it consists of a rigid portion 65 connected to the left hand side and an end portion 66 connected to the right hand side. The rigid portion 65 is formed by a cylindrical element having a number of slits 67 parallel to the axis of the instrument and regularly spaced around the circumference of the portion 65. The end portion 66 comprises a cylindrical bush 68 provided with a ring flange 69 forming a spherical flange.

The right hand side of the instrument is further composed of two actuating members 70 and 71. The actuating member 70 is a hollow tube like element comprising a ball shaped member 72, a tube 73 and a spherical flange 74. The ball shaped member 72 fits into the spherical flange 69 and in this way the member 70 is rotatably connected to the left hand part of the instrument. The ball shaped member 72 is provided with an annular flange surrounding the same and having two sets of openings, a first set positioned along a circle line around the flange 75 and a second set also positioned along a circle line around the flange 75, the circle line of the first set preferably having a same diameter as the circle line of the second set. The actuating member 71 is also a hollow tube like element comprising a ball shaped member 76 and a tube 77. The ball shaped member 76 is comparable to the ball shaped member 72 and fits into the spherical flange 74 whereby the member 71 is rotatably connected to the member 70. The ball shaped member 76 is provided with an annular flange 78 surrounding the same and provided with a set of openings positioned along a circle line around the flange 78.

The left hand part of the first intermediate layer or cylindrical element 2 comprises the longitudinal elements of the portion 23. In the right hand part with respect to the line A-A, these longitudinal elements are guided through some of the slits 67, through the first set of openings in the flange 75 and into the openings in the flange 78 to which they are connected. The left hand part of the second intermediate layer or cylindrical element 3 comprises the longitudinal elements of the portion 35. In the right hand part with respect to the line A-A these longitudinal elements are guided through some of the slits 67 into the second set of openings in the flange 75 to which they are connected.

The operation of the instrument shown in FIG. 5 is comparable to the operation of the instrument of FIG. 1. Any bending movement of the member 70 with respect to the flange 69 is translated into a bending movement of the zone 54, and any bending movement of the member 71 with respect to the flange 74 is translated into a bending movement of the zone 52. As a result of the fact that the longitudinal elements controlling the bending are connected to the actuating members 70 and 71 at points having a greater distance to the longitudinal axis of the instrument than the corresponding elements at the other end of the instrument, the bending movement of the members 70 and 71 is amplified into a bigger bending movement of the zones 54 and 52 respectively, and as such its operation is comparable to that of the instrument of FIG. 4.

Figure 6:
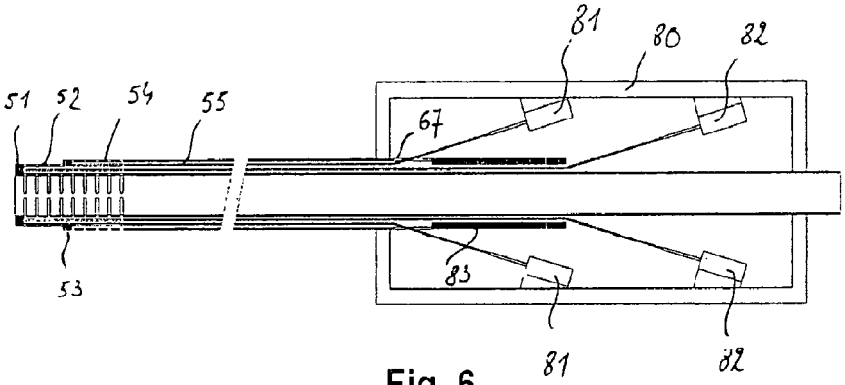

In the embodiment shown in FIG. 6 the handling end portion is identical to the handling end portion of the embodiment shown in FIG. 5, whereas the actuating end portion has been modified. Around the actuating end portion there is provided a cylindrical housing 80 which is mounted on the external layer of the instrument. Furthermore the external layer of the instrument at the actuating end portion side is provided with a cylindrical member 83 such that between the zone 55 and the cylindrical member 83 a number of slits 67 are present as shown in FIG. 5. To the inner wall of the cylindrical housing 80 there are mounted two sets of linear actuators 81 and 82 respectively. A linear actuator is a device which can cause a translation movement of an element such as for example the longitudinal elements in this type of endoscopic instruments. Such linear actuators are generally known in the art and will not be described in more detail here, and they can be controlled by electronic devices such as computers.

The longitudinal elements of the outer intermediate layer are passing through the slits 67 and connected to the set 81 of linear actuators. The longitudinal elements of the inner intermediate layer are passing through the cylindrical member 83 and connected to the second set 82 of linear actuators. By means of a correct actuation of the linear actuators 81 and 82 the orientation of the flexible zones 52 and 54 can be changed so that the same effects obtained as with the instrument according to FIG. 5 or FIG. 1, which means that more curves can be made by the handling end portion. It is necessary that the actuation of the different linear actuators is done in a controlled manner as otherwise the change of orientation cannot be performed. This means that if one actuator 81 is exerting a pulling force on its longitudinal element, the other actuators must be acting in a corresponding way, which means either exerting a smaller pulling force or exerting a pushing force so that the whole is in balance. The same applies if both sets of actuators are activated simultaneously.

Figure 7:
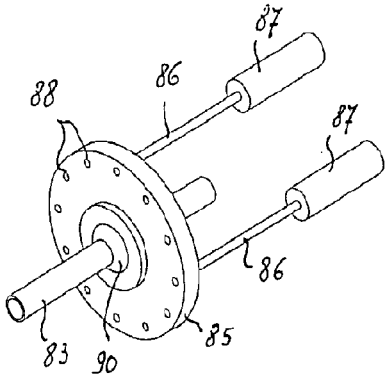

In case the number of longitudinal elements is larger than three which is mostly required to have a smooth transition of the movement of the actuating end portion to the handling end portion, the electronic control of all linear actuators may become complicated. In the FIGS. 7 and 8 there are shown two solutions for such a system. In the embodiment of FIG. 7 a disc 85 is mounted movable on the cylindrical element 83 by means of a ball bearing 90. The disc 85 is provided with a number of openings 88 along its outer circumference and the longitudinal elements are connected to the disc through these openings. As such the operation of the disc 85 is comparable to that of the disc 75 in FIG. 5. Two of the openings 88 are connected through elements 86 to a linear actuator 87. If the two openings 88 are not diametrically opposed to each other with respect to the axis of the cylindrical member 83, the movement of the two actuators 87 is sufficient to control fully the orientation of the disc 85 and thereby the movement imposed on the corresponding zone of the handling end portion.

Figure 8:
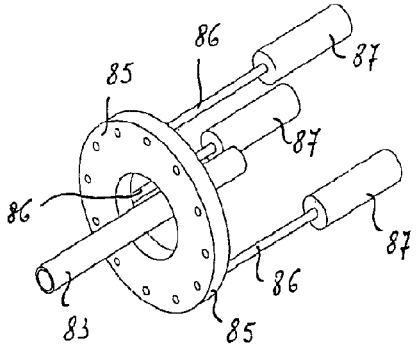

In the embodiment shown in FIG. 8 the disc 85 is not supported by a ball bearing on the cylindrical member 83, but three of the openings 88 are through elements 86 connected to linear actuators 87 and also supported by that. These three actuators 87 are controllable to fully control the orientation of the disc 85 and thereby the movement of the corresponding zone of the handling end portion.

In this way the electronic control of the longitudinal elements through linear actuators is reduced to the electronic control of either three or two s such actuators which is less complicated than the full control of all longitudinal elements.

A possible medical application of such instrument is shown in FIGS. 16 and 17. In this application one tubular feed through can be used to enter a body through one incision or hole. Through this feed through multiple endoscopic instruments having a body as per the invention can be passed trough channels that are parallel without space between those channels as is illustrated in FIG. 17. When a tubular feed trough like this is used for instruments as described in EP-A-1 708 609 it is not possible to manipulate the handling end portions of these instruments such that the longitudinal axes through the handling ends cross through the same point. Therefore these instruments strongly limit the application and freedom to act of the operator of the instruments. When instruments are used as per the invention, it is possible to maneuver the handling tips such that both instruments can be simultaneously used in which for example one instrument could hold tissue and the other instrument could cut free this tissue. The strong advantage of the invention therefore is that it enables the use of multiple instruments, without strong limitations to maneuverability and simultaneous use and that these instruments can be used as such through only one access opening in the body.

When expanding the idea of a system of having more than one system of longitudinal elements and having a corresponding number of flexible portions it is possible to even make more complicated curves.

Figure 9:
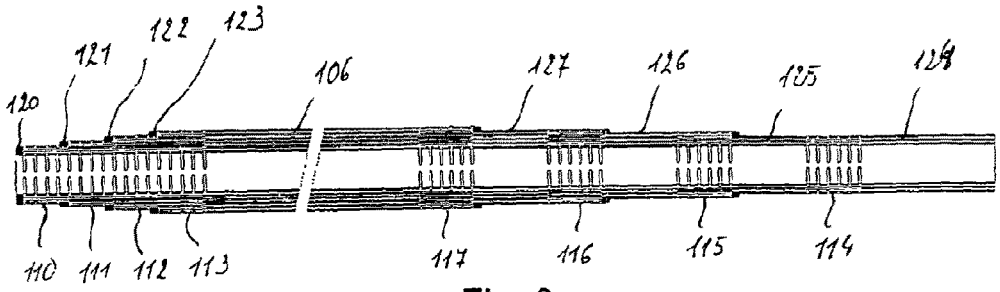

In FIG. 9 there is shown an instrument according to the invention which is composed of six layers, allowing the instrument with a handling portion which can be curved in a more complicated way as shown in the FIGS. 10, 11, 12 and 13. The basic construction shown in FIG. 1 has been maintained, in that this instrument has an inner and an outer layer 100 and 106 comparable to the inner and outer layer 11 and 14 of FIG. 1, except that the number of flexible portions has been increased taking into account the number of intermediate layers. In this way the handling end portion has been provided with four flexible portions, whereas the actuation portion also has four flexible portions. The flexible portions in the handling end portion are separated by very short rigid portions as in the embodiment of FIG. 1, and the flexible portions in the actuation end portions can be separated by longer rigid portions. By connecting the different rigid portions in the handling end portion with the corresponding rigid portions in the actuation end portion by means of longitudinal elements, the different flexible portions in the handling end portion can be bended in accordance with the bending of the flexible portions in the actuation end portion.

Figure 10:
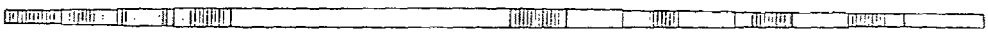
Figure 11:
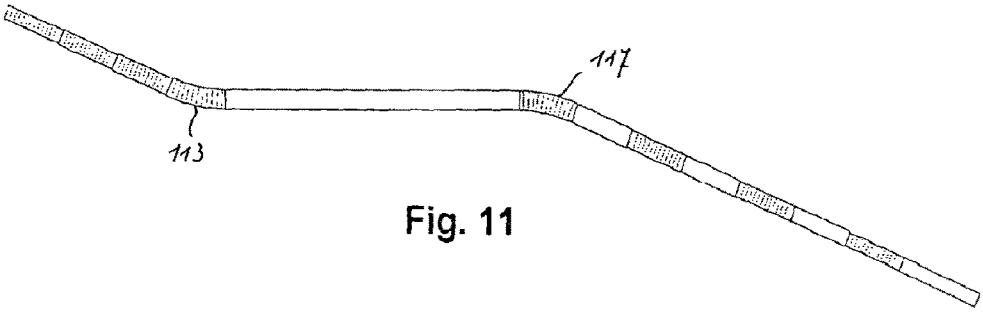
Figure 12:
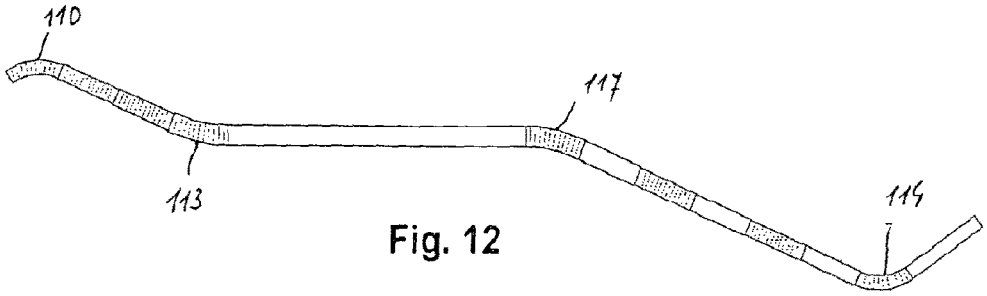
Figure 13:
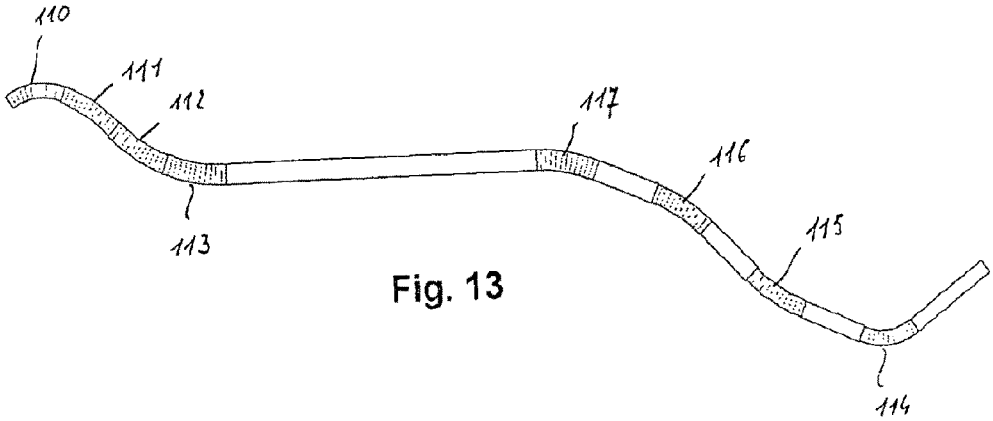

The operation is shown in the FIGS. 10, 11, 12 and 13. In FIG. 10 the instrument is shown in its starting position or shape. In FIG. 11 the flexible portion 113 has been bended over a defined degree by means of a bending of the flexible portion 117. By an additional bending of the flexible portion 114, the flexible portion 110 has been curved over a defined degree whereby the shape or configuration as shown in FIG. 12 has been obtained. When subsequently defined curves have been applied to the flexible portions 115, 116, corresponding curves can be obtained in the flexible portions 111, 112, resulting ultimately in the configuration shown in FIG. 13. Here is it must be remarked that the different curves made to the flexible portions 114, 115, 116 117 need not to be in the same plane, but that the plane of bending may be different for each flexible portion, whereby the curves obtained in the flexible portions 110, 111, 112 and 113 are also positioned in different planes. In this way it becomes possible to give complex configurations to handling end portions. This may be very important in all applications where it may be required to follow well defined paths in order to reach defined locations. It is obvious that also in case of more than four layers it is possible to use actuation and amplification such as described as in FIGS. 4, 5, 6, 7 and 8.

Theoretically an instrument can be made with an indefinite number of bending portions and corresponding layers, and as the number of layers will increase the possibilities of performing complicated curves will increase. However as the number of layers will increase also the outer diameter of the instrument will become bigger, specially in the case where the internal diameter of the instrument needs to have a defined minimal dimension required by the function to be performed by the instrument. Also as the number of layers increases, the stiffness of the flexible portions will increase, especially of the more proximal portions. Such an increase of stiffness and outer diameter of the instrument will hinder its application and ultimately will make it useless.

In order to have an instrument with an increased bending capacity without increasing the diameter or stiffness to unacceptable proportions, it is possible to combine the different longitudinal elements to be used for actuating the bending of the different flexible portions in the handling portion into one and the same layer, whereby the number of layers is substantially reduced. This is possible because it is only necessary to have three longitudinal elements for fully controlled actuation of one flexible portion. Therefore a layer consisting out of for example 12 longitudinal elements can be used for actuating 4 flexible portions. In FIGS. 14, 15, 18 and 19 there are shown instruments that are equivalent to an instrument having multiple layers that actuate multiple flexible portions at each end, but where there is only a reduced number of layers in that these intermediate layers contain groups of 3 longitudinal elements.

Figures 14, 15:
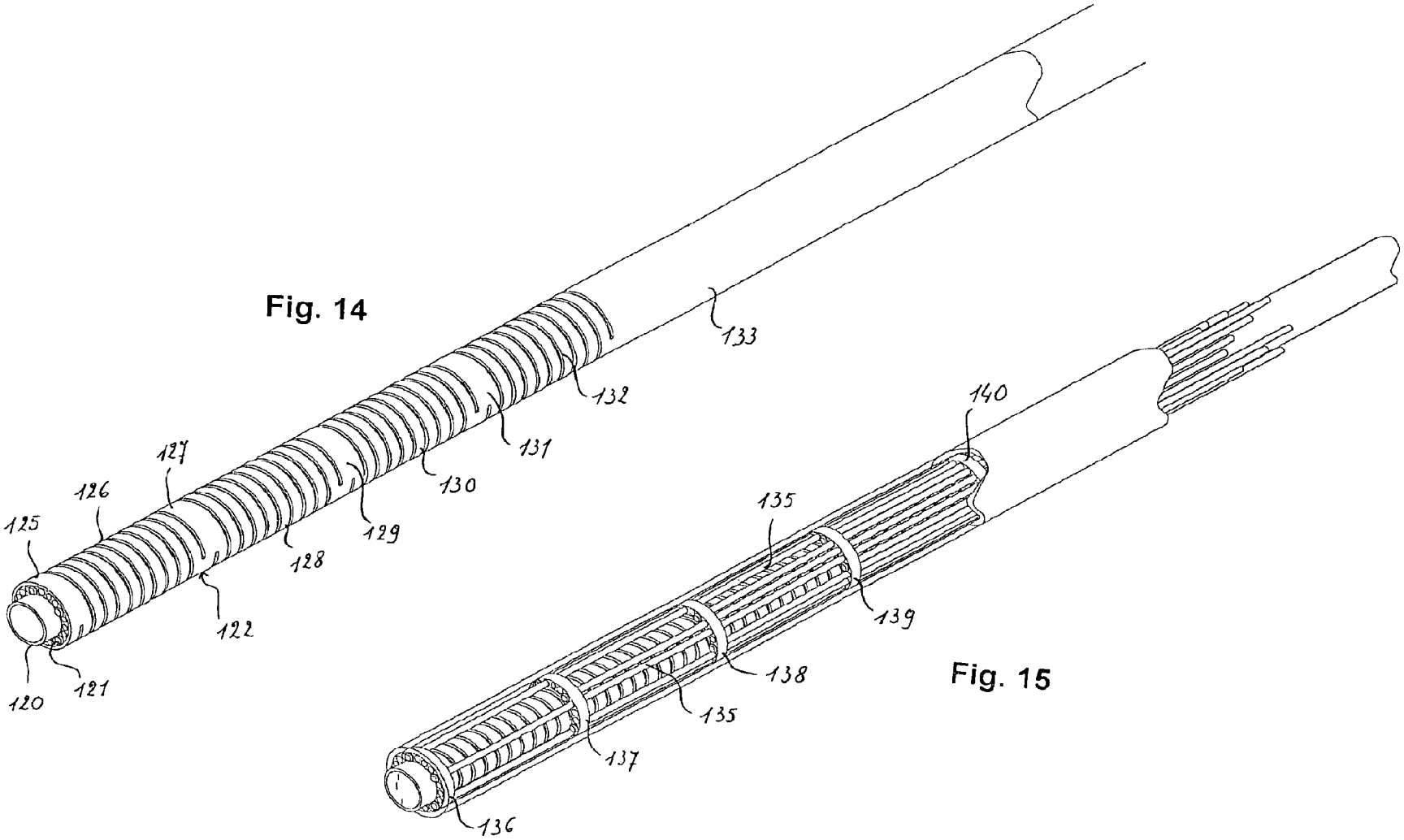

A first embodiment of such an instrument is shown in the FIGS. 14 and 15 that show the handling end portion of such an instrument only. It is obvious that the actuating end portion could be identical to the various actuating end portions as described above. As shown the instrument of FIGS. 14 and 15 is composed of three layers, an inner layer or cylindrical element 120, an intermediate layer 121 and an outer layer or cylindrical element 122. As seen along the longitudinal direction the instrument has a rigid end zone 125 forming the handling end portion, a flexible zone 126, a rigid zone 127, a flexible zone 128, a rigid zone 129, a flexible zone 130, a rigid zone 131, a flexible zone 132 and a rigid zone 133. At the actuating end portion (not shown), the instrument has corresponding zones comprising alternating flexible and rigid zones comparable to the instrument shown in FIG. 9 and of constructions as described above.

The inner and outer layer 120 and 122 are continuous cylindrical elements with rigid and flexible portions which may be obtained as described in the European patent application 08 004 373.0. The intermediate layer 121 comprises a number of longitudinal elements 135 (see FIG. 15) which are all parallel to the longitudinal axis of the instrument and a number of rigid rings 136, 137, 138, 139 and 140. Each of the rings 136-140 is provided with a number of openings extending in the longitudinal direction parallel to the axis of the instrument, through which the longitudinal elements 135 can pass. The rigid rings 136-140 are coinciding with the rigid zones 125, 127, 129, 131 and the beginning part of the rigid portion 133.

The longitudinal elements 135 are divided into four groups, each group comprising at least three longitudinal elements 135 which are preferably regularly spaced along the circumference of the intermediate layer 121. The first group of longitudinal elements 135 has its ends connected to the rigid ring 136 and the elements are further guided through openings in the other rings 137-140. The second group of longitudinal elements 135 has its ends connected to the rigid ring 137 and the elements are further guided through the openings in the rings 138-140. The third group of longitudinal elements 135 has its ends connected to the rigid ring 138 and the elements are further guided through the openings in the rings 139 and 140. The fourth group of longitudinal elements 135 has its ends connected to the rigid ring 139 and the elements are further guided through the openings in the ring 140. The rings 136-140 are connected to at least one of the inner and outer layer 120 and 122.

As a result of the fact that there are four groups of longitudinal elements each acting on a different part of the handling end portion of the instrument, this instrument is exactly comparable to the instrument of FIG. 9 in which there are four bending possibilities for the handling end portions which can be operated through the bending of the corresponding parts in the actuating end portion or by four groups of actuators in the actuating end portion as in FIG. 6, 7 or 8. The improvement of this embodiment is especially the use of one layer combining the different groups of longitudinal elements whereby the diameter and the flexibility of the instrument of FIG. 14 become smaller than of the instrument of FIG. 9.

Figures 18, 19:
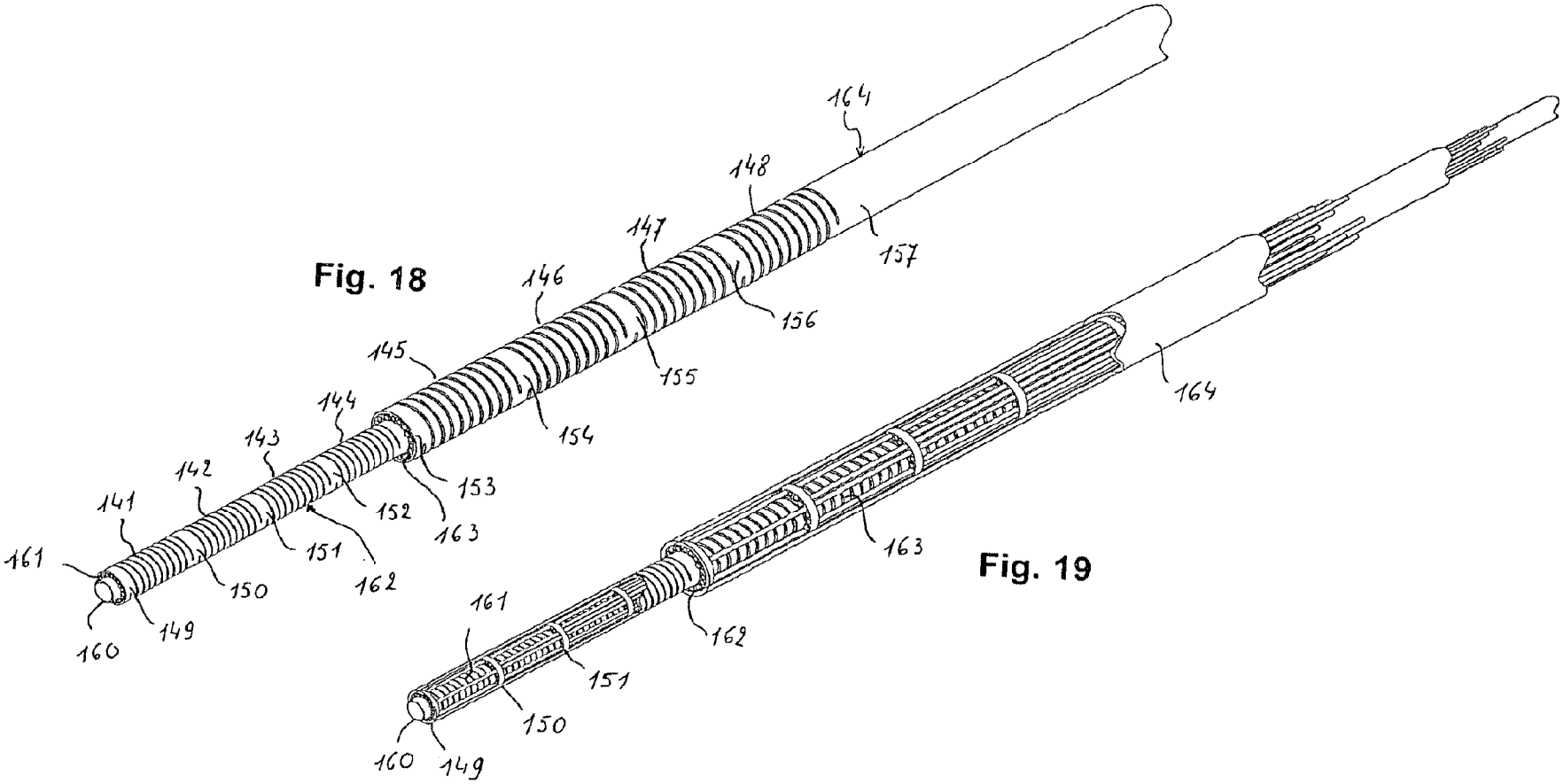
Figure 20A:
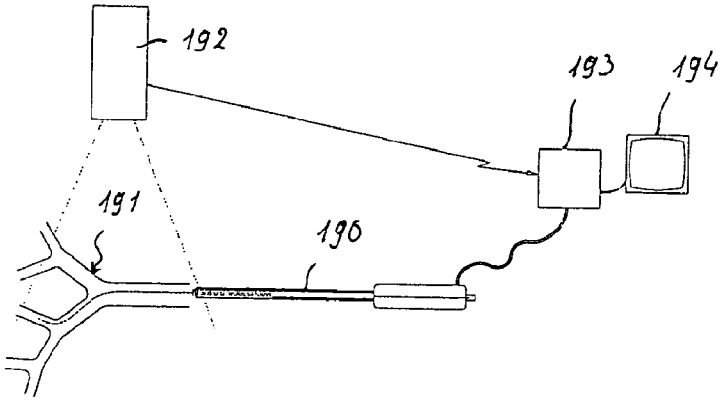
Figure 20B:
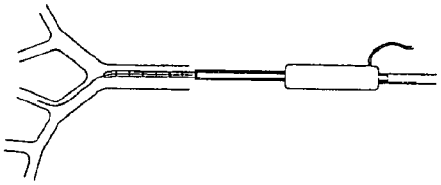
Figure 20C:
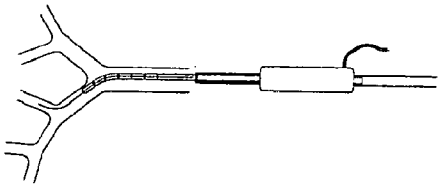
Figure 20D:
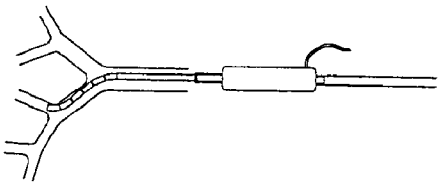
Figure 21A:
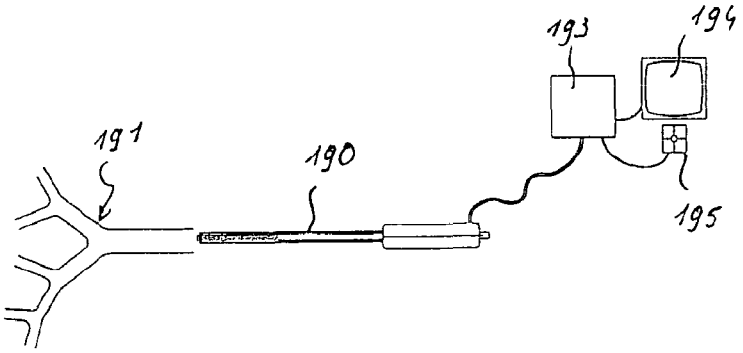
Figure 21B:
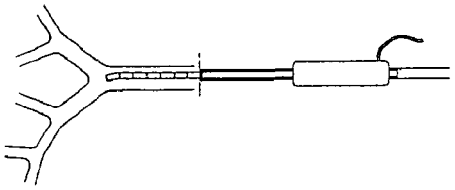
Figure 21C:
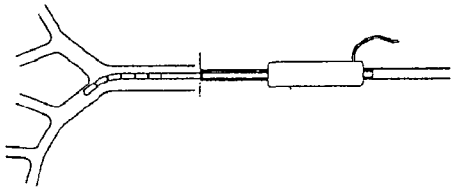
Figure 21D:
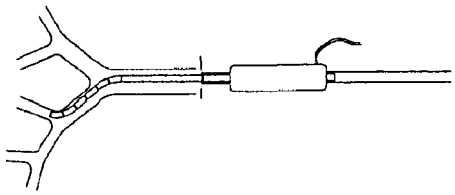

In FIGS. 18 and 19 there is shown an instrument in which the principle of having more than one group of longitudinal elements in one layer has been applied for an instrument which is comparable to an instrument having eight layers of longitudinal elements for transferring bending movement from the actuating end portion to the handling end portion. Actually the instrument of FIGS. 18 and 19 has two intermediate layers each comprising four groups of longitudinal elements.

In the handling end portion shown in FIGS. 18 and 19 the instrument has eight flexible zones 141-148 and nine ring zones 149-157 defining the different bending zones. The first four flexible zones 141-144 are controlled by means of longitudinal elements contained in the first or inner intermediate layer, whereas the second four flexible zones 145-148 are controlled by means of longitudinal elements contained in the second or outer intermediate layer. The instrument has in fact five layers, an inner continuous layer 160, a first or inner intermediate later 161 containing the first group of longitudinal elements, an intermediate continuous layer 162, a second outer intermediate layer 163 containing the second group of longitudinal elements and an outer continuous layer 164. The layers 160, 162 and 164 are standard layers or cylindrical elements consisting of flexible and rigid portions as defined above. The zones 141-144 and 149-153 do not have to be surrounded by the layers 163 and 164 but could be surrounded by an extended flexible portion of outer layer 164 to form an uniform outer diameter.

The actuating end portion can be of any construction as described above as long as the number of actuated flexible zones corresponds to the number of handling end flexible zones. The operation of this embodiment is comparable to an instrument having eight layers of longitudinal elements, implying a total of ten layers. Because of the combination of four groups of longitudinal elements in one layer each, the number of layers has been reduced to five with a corresponding reduction of the diameter and stiffness. Nevertheless this instrument allows eight simultaneous but independent bending operations to be performed by the instrument, thereby expanding the possibilities of its use without a substantial increase of the diameter and stiffness.

Obviously any combination of the number of layers, longitudinal elements per layer and number of longitudinal elements per group can be made to obtain the optimal solution for various applications.

In the FIGS. 16 and 17 there is shown how the instrument according to the invention can be used in a convenient way, while at the same time the penetration in the working area can be restricted to a single tube section. This is especially important in applications where the target to be handled can only be approached through only one single way, which is for example the case in a number of surgical treatments.

In the FIGS. 16 and 17 there is shown an external tube 170 which is used as a guiding tube for a number of endoscopic instruments. The external tube 170 comprises a single tube section 171 which extends up till the line B-B in FIG. 16. Above this line the external tube 170 is composed of a central tube section 172 and two branch tube sections 173 and 174, which are merging together at the level of the line B-B. The single tube section 171 is the part of the external tube used for penetration. In the embodiment shown, five endoscopic instruments are inserted into the external tube 170, three through the central tube section 172 and one through each of the branch tube sections 173, 174. The endoscopic instrument 175 is for example a viewing pipe, whereas the endoscopic instruments 176 and 177 are used for the supply and/or discharge of gasses and/or liquids to and from the target area. The endoscopic instruments 178 and 179 are according to the invention with multiple orientation possibilities and are used as instruments for performing some operations in the target area. In order to allow access through the branch tube sections 173 and 174, the intermediate zone of thee instruments between the handling end portion and the actuating end portion must be flexible as well, so that they can follow the curved profile of the branch tube sections. In view of the multiple orientation possibilities of each of the instruments 178 and 179 it becomes possible to allow these instruments to work on the same spot in the target area without interfering with each other as shown in the FIG. 16.

The external tube 170 may be a rigid tube, but it is also possible to use at least for the section 171 a flexible tube with multiple bending possibilities comparable to the instrument according to the invention. The same applies to the endoscopic instruments 175, 176 and 177. In the embodiment shown they have the shape of a rigid tube, but it may be flexible instruments according to the invention with multiple bending possibilities.

In the FIGS. 20 and 21 there is shown schematically two important applications of the instrument according to the invention in which the multiple orientation possibilities are used. It is accepted that an instrument 190 according to the invention must be introduced in a canal system 191, which system is very sensitive to contact with the instrument or parts thereof so that the contact between the instrument and the canal walls must be avoided as much as possible. Such a canal system may be present in the human body such as for example the human lung, but it may also be a technical instrument with sensitive components which must be serviced.

In FIG. 20 it is accepted that the geometry of the canal system 191 has already been mapped by means of an imaging technique and stored in an electronic device 192. The information of the device 192 is transferred to the control system 193 which is used to define the orientation of the different zones of the handling end portion of the instrument at any moment that the instrument is introduced in the canal system. The system 193 is therefore connected to the actuating end portion of the instrument 190. For safety reasons a viewing system is also connected to the control system 193 whereby the actual situation at the handling tip of the instrument can be followed. Upon introduction of the instrument in the canal system 191, the actual position of the handling tip is controlled and based upon the information stored in the device 192 and the actual position of the handling tip the orientation of the different zones in the handling end portion is controlled so that the handling end portion of the instrument is following exactly the predetermined itinerary through the canal system 191, such as shown in the FIGS. 20B, 20C and 20D. This may be dynamic process in which each time that the handling tip is progressing further in the canal system, the orientation of the different zones of the handling end portion is readjusted automatically, thereby avoiding contact between the instrument and the canal walls.

In the embodiment shown in FIG. 21 it is accepted that the canal system 191 has not been mapped and stored. In this situation the handling tip must be controlled by means of the viewing system 194. For that purpose a joy stick 195 has been provided by means of which the orientation of the flexible zones of the handling end portion can be controlled. Each time the handling tip is progressing the orientation of all the zones is controlled by means of the joy stick 195 and information stored in the device 193 about the way along which the instrument has already progressed in the canal system 191. In this way also the contact between the instrument and the canal walls can be avoided or at least substantially reduced.

It is obvious that the invention is not restricted to the described embodiments as shown in the annexed drawings, but that within the scope of the claims modifications can be applied without departing from the inventive concept.

The invention claimed is:

1. An instrument for at least one of endoscopic applications, mechanical applications, and electronic applications, comprising a tube like member having a handling end portion having at least a first rigid zone, a first flexible handling portion, a second rigid zone and a second flexible handling portion, and having actuating means located at an *other,* actuating end portion, [said tube like member comprising] at least an inner cylindrical element, [a first] *an* outer cylindrical element and *a* first *cylinder, said inner cylindrical element, outer cylindrical element and first cylinder being coaxially arranged, the first cylinder comprising* longitudinal elements[, said first longitudinal elements being located in a first intermediate layer between said inner cylindrical element and said first outer cylindrical element and being connected to both the actuating means and to the handling end portion] for transferring a movement of the actuating means to the handling end portion resulting in a change of orientation [thereof, wherein the actuating means have at least a first and a second actuating means and the first longitudinal elements comprise at least a first and second set of longitudinal elements, the first set of longitudinal elements having respective handling ends connected to a first rigid ring, said first rigid ring being connected to at least one of said inner cylindrical element and said first outer cylindrical element in said first rigid zone, the second set of longitudinal elements having respective handling ends connected to a second rigid ring, said second rigid ring being connected to at least one of said inner cylindrical element and said first outer cylindrical element in said second rigid zone, and said first set of longitudinal elements being guided through openings in said second rigid ring, the first actuating means being connected to an actuating end of said first set of longitudinal elements, and the second actuating means being connected to an actuating end of said second set of longitudinal elements,] *of at least one of the first flexible handling portion and the second flexible handling portion, said longitudinal elements being formed by portions of the first cylinder, and* wherein said inner cylindrical element and said [first] outer cylindrical element are continuous cylindrical elements[, ] each of which having a tube wall that comprises rigid and flexible portions that coincide with respective ones of said first rigid zone, said first flexible handling portion, said second rigid zone and said second flexible handling portion, [and] wherein said flexible portions are obtained by locally providing slits in the respective tube walls of said inner cylindrical element and said [first] outer cylindrical element.

2. The instrument according to claim 1, wherein [said handling end portion also has a third rigid zone, a third flexible handling portion, a fourth rigid zone and a fourth flexible handling portion, wherein the actuating means have a third and a fourth actuating means and the first longitudinal elements comprise a third and fourth set of longitudinal elements, the third set of longitudinal elements having respective handling ends connected to a third rigid ring, said third rigid ring being connected to at least one of said inner cylindrical element and said first outer cylindrical element in said third rigid zone, the fourth set of longitudinal elements having respective handling ends connected to a fourth rigid ring, said fourth rigid ring being connected to at least one of said inner cylindrical element and said first outer cylindrical element in said fourth rigid zone, said first set of longitudinal elements being also guided through openings in said third and fourth rigid ring, said second set of longitudinal elements being guided through openings in said third and fourth rigid ring, said third set of longitudinal elements being guided through openings in said fourth rigid ring, the third actuating means being connected to an actuating end of said third set of longitudinal elements, and the fourth actuating means being connected to an actuating end of said fourth set of longitudinal elements] *the actuating means comprises a tube like section containing a number of alternating flexible and rigid actuating zones, said longitudinal elements are arranged in sets, and each set of longitudinal elements is connecting one of the rigid actuating zones with a corresponding flexible handling portion.*

3. The instrument according to claim [1] *2*, wherein each set [of said first and second sets] of longitudinal elements comprises at least three longitudinal elements.

4. The instrument according to claim 1, wherein [each element of the first longitudinal elements is cable shaped] *the instrument comprises a second cylinder arranged coaxially with the inner cylindrical element, outer cylindrical element, and first cylinder, said longitudinal elements are arranged in sets, each set of said longitudinal elements being configured to control said change of orientation of one flexible handling portion, and several sets of longitudinal elements are located in at least one of the first and second cylinders.*

5. The instrument according to claim 1, wherein [the handling end portion has at least a third rigid zone, a third flexible handling portion, a fourth rigid zone and a fourth flexible handling portion, said tube like member comprising a second outer cylindrical element outside of said first outer cylindrical element, and second longitudinal elements, said second longitudinal elements being located in a second intermediate layer between said first outer cylindrical element and said second outer cylindrical element and being connected to both the actuating means and to the handling end portion for transferring a movement of the actuating means to the handling end portion resulting in a change of orientation thereof, wherein the actuating means have at least a third and a fourth actuating means and the second longitudinal elements comprise at least a third and fourth set of longitudinal elements, the third set of longitudinal elements having respective handling ends connected to a third rigid ring, said third rigid ring being connected to at least one of said first outer cylindrical element and said second outer cylindrical element in said third rigid zone, the fourth set of longitudinal elements having respective handling ends connected to a fourth rigid ring, said fourth rigid ring being connected to at least one of said first outer cylindrical element and said second outer cylindrical element in said fourth rigid zone, and said third set of longitudinal elements being guided through openings in said fourth rigid ring, the third actuating means being connected to an actuating end of said third set of longitudinal elements, and the fourth actuating means being connected to an actuating end of said fourth set of longitudinal elements] *the instrument comprises a second cylinder arranged coaxially with the inner cylindrical element, outer cylindrical element, and first cylinder, said longitudinal elements are arranged in sets, each set of said longitudinal elements being configured to control said change of orientation of one flexible handling portion, and each set of longitudinal elements is located in a separate one of the first and second cylinders.*

[6. The instrument according to claim 5, wherein each set of said third and fourth sets of longitudinal elements comprises at least three longitudinal elements.]

[7. The instrument according to claim 5, wherein each element of the second longitudinal elements is cable shaped.]

8. The instrument according to claim 1, wherein the tube like section of the actuating means has a diameter which is different from the diameter of the remaining tube like member.

9. The instrument according to claim 1, wherein *the actuating means* at the actuating end portion *comprises at least one rigid disc, said longitudinal elements are arranged in sets, each set of said longitudinal elements being configured to control said change of orientation of one flexible handling portion, and* at least one set of longitudinal elements is connected to [a] *said at least one* rigid disc *of which* the orientation [of which] can be changed with respect to a plane perpendicular to [the] *a* longitudinal axis of the instrument.

10. The instrument according to claim 9, wherein the *at least one* rigid disc is mounted on a ball-and-socket joint connected to the instrument and in that the orientation of the *at least one rigid* disc is controlled by means of two linear actuators.

11. The instrument according to claim 9, wherein the rigid disc is supported by means of three linear actuators.

12. The instrument according to claim 1, wherein the [actuating end portion comprises a plurality of alternating flexible and rigid zones, said plurality corresponding in number to the number of flexible and rigid zones in said handling end portion] *the actuating means at the actuating end portion comprises at least one set of linear actuators, said longitudinal elements are arranged in sets, each set of said longitudinal elements being configured to control said change of orientation of one flexible handling portion, and at least one set of longitudinal elements is connected to said at least one set of linear actuators.*

*13. The instrument according to claim 1, wherein the instrument is flexible between the handling end portion and the actuating end portion.*

*14. A system comprising a guiding tube and two instruments for at least one of endoscopic applications, inspection and reparation of mechanical or electronic installations,*

*said guiding tube comprising a number of guiding tube sections, two of the guiding tube sections having a curved profile,*

*each of the two instruments comprising a tube like member having a handling end portion having at least a first rigid zone, a first flexible handling portion, a second rigid zone, and a second flexible handling portion and actuating means located at an other, actuating end portion, at least an inner cylindrical element, an outer cylindrical element, and a first cylinder, said inner cylindrical element, outer cylindrical element, and first cylinder being coaxially arranged, the first cylinder comprising longitudinal elements for transferring a movement of the actuating means to the handling end portion resulting in a change of orientation of at least one of the first flexible handling portion and second flexible handling portion, said longitudinal elements being formed by portions of the first cylinder, each of the two instruments being flexible between the handling end portion and the actuating end portion such that they can be inserted into one of said guiding tube sections with said curved profile, and said inner cylindrical element and outer cylindrical element being continuous cylindrical elements each one having a tube wall comprising rigid and flexible portions that coincide with respective ones of said first rigid zone, said first flexible handling portion, said second rigid zone and said second flexible handling portion, and wherein the outer cylindrical element and the inner cylindrical element are tubes having tube walls and the flexible portions are obtained by locally providing slits in the respective tube walls of said outer cylindrical element and inner cylindrical element.*

*15. A system comprising an instrument for at least one of endoscopic applications, inspection and reparation of mechanical or electronic installations, comprising a tube like member having a handling end portion having at least a first rigid zone, a first flexible handling portion, a second rigid zone, and a second flexible handling portion and actuating means located at an other, actuating end portion, at least an inner cylindrical element, an outer cylindrical element, and a first cylinder, said inner cylindrical element, outer cylindrical element, and first cylinder being coaxially arranged, the first cylinder comprising longitudinal elements for transferring a movement of the actuating means to the handling end portion resulting in a change of orientation of at least one of the first flexible handling portion and the second flexible handling portion, said longitudinal elements being formed by portions of the first cylinder, the system also comprising a control system connected to the actuating means and configured to control said change of orientation of the first and second flexible handling portions, and said inner cylindrical element and outer cylindrical element being continuous cylindrical elements each one having a tube wall comprising rigid and flexible portions that coincide with respective ones of said first rigid zone, said first flexible handling portion, said second rigid zone and said second flexible handling portion, and the flexible portions are obtained by locally providing slits in the respective tube walls of said outer cylindrical element and inner cylindrical element.*

*16. The system according to claim 15, wherein said control system is connected to an electronic device storing geometry data of a canal system in which said instrument is*

*to be introduced, and the control system is configured to control the handling end portion of the instrument upon introduction in said canal system.*

*17. The system according to claim 15, wherein said control system is equipped with a joy stick by means of which the orientation of the handling end portion can be controlled.*

* * * * *